United States Patent
Maignan et al.

(10) Patent No.: US 6,475,495 B1
(45) Date of Patent: *Nov. 5, 2002

(54) HYPERBRANCHED POLYMERS OR DENDRIMERS CONTAINING A PARTICULAR GROUP, PREPARATION PROCESS, USE AND COMPOSITIONS COMPRISING THEM

(75) Inventors: Jean Maignan, Tremblay en France (FR); Sylvie Genard, Paris (FR)

(73) Assignee: L'Oreal, S.A., Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 09/581,767

(22) PCT Filed: Nov. 26, 1998

(86) PCT No.: PCT/FR98/02538

§ 371 (c)(1),
(2), (4) Date: Jun. 23, 2000

(87) PCT Pub. No.: WO99/32540

PCT Pub. Date: Jul. 1, 1999

(30) Foreign Application Priority Data

Dec. 19, 1997 (FR) .............................. 97 16176

(51) Int. Cl.[7] .......................... A61K 7/00; A01N 63/00; C08F 283/00; C08G 75/00
(52) U.S. Cl. .......................... 424/401; 424/88; 525/523; 528/373
(58) Field of Search ................... 424/88, 401, DIG. 16; 528/373; 525/523

(56) References Cited

U.S. PATENT DOCUMENTS

| | | | | |
|---|---|---|---|---|
| 4,882,399 A | * | 11/1989 | Tesoro et al. ............... | 525/523 |
| 4,886,663 A | * | 12/1989 | Houghten .................... | 424/88 |
| 5,362,478 A | * | 11/1994 | Desai et al. .................. | 424/9 |
| 5,627,045 A | * | 5/1997 | Bochner et al. .............. | 435/34 |
| 5,646,239 A | * | 7/1997 | Constancis et al. ......... | 528/373 |
| 6,020,457 A | * | 2/2000 | Klimash et al. ............. | 528/373 |
| 6,068,835 A | * | 5/2000 | Franzke et al. ......... | 424/70.11 |

FOREIGN PATENT DOCUMENTS

| | | |
|---|---|---|
| EP | 0 556 871 | 8/1993 |
| EP | 0 582 152 | * 2/1994 |
| EP | 0 736 297 | * 10/1996 |
| FR | 2 761 691 | 10/1998 |
| WO | WO 90/11778 | 10/1990 |

OTHER PUBLICATIONS

Toru Takagishi et al., "Macromolecule–Small Molecule Interactions; Introduction of Additional Binding Sites in Polyethyleneimine by disulfide Cross–linkage", Biopolymers, vol. 11, No. 2, 1972, pp. 483–491.

English language Derwent Abstract of FR 2 761 691., Oct. 1998.

* cited by examiner

*Primary Examiner*—Michael G. Hartley
*Assistant Examiner*—Michael A. Willis
(74) *Attorney, Agent, or Firm*—Finnegan, Henderson, Farabow, Garrett & Dunner, LLP

(57) ABSTRACT

The invention concerns a compound selected among hyperbranched polymers and dendrimers, characterised in that it comprises at least one group of formula (I). The invention also concerns a method for preparing said compounds, and their use as thickening or gelling agent, in particular in cosmetics or pharmaceutics. The invention further concerns a cosmetic or pharmaceutical composition containing, in a cosmetically or pharmaceutically acceptable medium, said compounds.

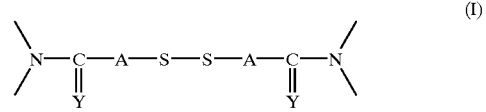

37 Claims, No Drawings

HYPERBRANCHED POLYMERS OR DENDRIMERS CONTAINING A PARTICULAR GROUP, PREPARATION PROCESS, USE AND COMPOSITIONS COMPRISING THEM

This application is a 371 of PCT/FA98/02538, filed Nov. 26, 1998.

The present invention relates to novel compounds which can be used in cosmetics or in pharmaceuticals, in particular in dermatology, and which make it possible in particular to obtain thickened compositions, or even gelled compositions.

Hyperbranched polymers and dendrimers are well known in the prior art.

Hyperbranched polymers are molecular constructions having a branched structure, generally around a core. Their structure generally lacks symmetry, the base units or monomers used to construct the hyperbranched polymer can be of diverse nature and their distribution is non-uniform. The branches of the polymer can be of different natures and lengths. The number of base units, or monomers, may be different depending on the different branching. While at the same time being asymmetrical, hyperbranched polymers can have: an extremely branched structure, around a core; successive generations or layers of branching; a layer of end chains.

Hyperbranched polymers are generally derived from the polycondensation of one or more monomers ABx, and B being reactive groups capable of reacting together, x being an integer greater than or equal to 2, but other preparation processes may be envisaged. Hyperbranched polymers are characterized by their degree of polymerization DP=1−b, b being the percentage of non-terminal functionalities in B which have not reacted with a group A. Since the condensation is not systematic, in contrast with the synthesis of dendrimers, the degree of polymerization is less than 100%. An end group T can be reacted with the hyperbranched polymer to obtain a particular functionality on the ends of chains.

Several hyperbranched polymers can be combined together, via a covalent bond or another type of bonding, by means of their end groups. Such polymers, known as bridged polymers, fall within the definition of the hyperbranched polymers according to the present invention.

Dendrimers are highly branched polymers and oligomers having a well-defined chemical structure. As a general rule, dendrimers comprise a core, a given number of generations of branches, or spindles, and end groups. The generations of spindles consist of structural units which are identical for the same generation of spindles and which may be identical or different for different generations of spindles. The generations of spindles extend radially in a geometrical progression from the core. The end groups of a dendrimer from the Nth generation are the end functional groups of the spindles of the Nth generation or end generation.

The definition of dendrimers given above includes molecules containing symmetrical branching; it also includes molecules containing non-symmetrical branching, such as, for example, dendrimers whose spindles are lysine groups, in which the branching of one generation of spindles on the preceding generation takes place on the a and c amines of lysine, which leads to a difference in the lengths of the spindles of different branching.

Dense star polymers, starburst polymers and rod-shaped dendrimers are included in the present definition of dendrimers. The molecules known as arborols and cascade molecules also fall within the definition of dendrimers according to the present invention.

Several dendrimers can be combined together, via a covalent bond or another type of bonding, by means of their end groups to give species known as bridged dendrimers or dendrimer aggregates. Such species are included in the definition of dendrimers according to the present invention.

Dendrimers can be in the form of an assembly of molecules of the same generation, which are referred to as monodisperse assemblies; they can also be in the form of assemblies of different generations, known as polydisperse assemblies. The definition of dendrimers according to the present invention includes both monodisperse and polydisperse assemblies of dendrimers.

French patent application FR 97/04085 in the name of the Applicant in particular discloses novel polymers chosen from hyperbranched polymers and dendrimers, comprising functional groups corresponding to the following formula:

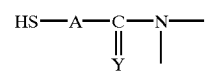

in which

Y represents an oxygen atom or an NH group,

A represents a linear, branched or cyclic, saturated or unsaturated $C_1$–$C_{12}$ alkanediyl group, this group optionally being interrupted with one or more hetero atoms and/or substituted with a function chosen from amino, acylamino, carboxylic acid and ester.

These polymers find an application in particular in cosmetics and dermatology as antioxidants or reducing agents.

Now, the Applicant has found, surprisingly, that the said polymers can also be used to allow the preparation of compositions, in particular cosmetic or pharmaceutical compositions, which are thickened or even gelled.

Thus, a subject of the present invention is a compound chosen from hyperbranched polymers and dendrimers, characterized in that it comprises at least one group of formula:

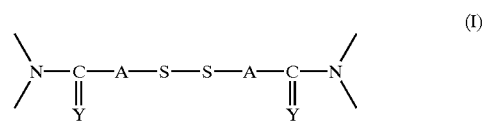

in which:

Y represents an oxygen atom or an NH group, and

A represents a linear, branched or cyclic, saturated or unsaturated $C_1$–$C_{12}$ alkanediyl group, this group optionally being interrupted with one or more hetero atoms and/or substituted with a function chosen from:
amino (—$NH_2$)
acylamino (—NH—CO—R) in which R represents a linear, branched or cyclic, saturated or unsaturated $C_1$–$C_{10}$ alkyl group,
carboxylic acid (—COOH),
ester (—COOR) in which R represents a linear, branched or cyclic, saturated or unsaturated $C_1$–$C_{10}$ alkyl group.

Another subject of the invention is a process for preparing the above compounds, in which a polymer is oxidized, this polymer being chosen from hyper-branched polymers and dendrimers comprising at least one group of formula (II):

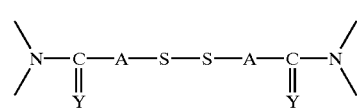

(I)

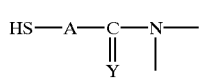

(II)

Another subject of the invention is the use of at least one compound as above, as a thickener or gelling agent, in particular in a cosmetic or pharmaceutical composition also comprising a cosmetically or pharmaceutically acceptable medium.

Another subject of the invention is a cosmetic or pharmaceutical composition comprising, in a cosmetically or pharmaceutically acceptable medium, at least one compound as defined above.

Another subject is the use of at least one polymer chosen from hyperbranched polymers and dendrimers comprising at least one group of formula (II), for the preparation of a composition comprising at least one compound as defined above.

The prior art discloses a certain number of common gelling agents or thickeners which can be used to modify the viscosity of compositions, in particular cosmetics. Mention may thus be made of algal extracts such as agar-agar, carrageenans and alginates; gums; seed extracts, plant exudates or microorganism exudates, and cellulose derivatives; fruit extracts such as pectins; gelling agents of animal origin such as gelatin, caseinates or water-soluble gelling synthetic polymers such as crosslinked polyacrylic acids.

However, these gelling agents have certain drawbacks. Specifically, the common gelling agents give gels or thickened media as soon as they are introduced into the said medium. They must thus necessarily be introduced into the medium before it is applied to the intended support.

Now, it has been found that by using the compounds according to the invention or a composition comprising them, it is possible to form the gel when desired, and in particular in situ, i.e. after the composition has been applied to the support.

Thus, it is possible to form the said gel before it has been packaged, and thus to have available a ready-to-apply gelled composition. In this case, the compounds according to the invention are used like common gelling agents.

However, it is also possible to prepare a composition which is not gelled because it is not oxidized, to package it in this form and to carry out the oxidation, and thus the gelation, only when the composition is applied to the support, for example by oxidation in the open air. This may be advantageous in particular in the case of haircare uses, such as styling gels or hair-colouring compositions.

Thus, the invention provides a system for gelling the composition before, during or after it has been applied to the support.

Another advantage of the invention lies in the tact that, in certain cases, it may be necessary to store separately two liquid solutions which need to be mixed together at the time of application, the viscosity of the resulting mixture needing to be increased before application. This is the case in particular for certain hair-colouring products. The compounds according to the invention allows these requirements to be satisfied.

The compounds which are the subject of the invention are thus chosen from hyperbranched polymers and dendrimers, and comprise at least one group of formula (I):

in which:
Y represents O or NH,
A represents a linear, branched or cyclic, saturated or unsaturated $C_1$–$C_{12}$ alkanediyl group, this group optionally being interrupted with one or more hetero atoms and/or substituted with a function chosen from:
amino (—$NH_2$) optionally in the form of a salt of an inorganic or organic acid,
acylamino (—NH—COR) in which R represents a linear, branched or cyclic, saturated or unsaturated $C_1$–$C_{10}$ alkyl group,
carboxylic acid (—COOH),
ester (—COOR) in which R represents a linear, branched or cyclic, saturated or unsaturated $C_1$–$C_{10}$ alkyl group.

Preferably, the compound according to the invention is chosen from hyperbranched polymers, and in particular polyethyleneimine, comprising at least one group of formula (I).

Preferably, Y represents an oxygen atom.
Preferably, the hetero atoms are chosen from oxygen and nitrogen (O and N).
Preferably, A is a methylene, ethylene, propylene, methylpropylene, ethylpropylene, tetramethylene, pentamethylene, hexamethylene, phenylene or phenyldiyl group.

Advantageously, A represents a radical corresponding to one of the formulae (a) to (d) below:
(a) —$CHR^1$—$CHR^2$—$CHR^3$—
(b) —$CHR'^1$—$CHR'^2$—$CHR'^3$—$CHR'^4$—

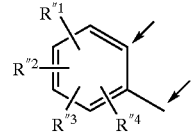

(c)

(d) —$(CHR'''^1)_k$—$(CHR'''^2)$—$CH(CO_2H)$—NH—
in which
$R^1$, $R^2$, $R^3$, $R'^1$, $R'^2$, $R'^3$ and $R'^4$, $R'''^1$ and $R'''^2$, which may be identical or different, represent: a hydrogen atom; a linear, branched or cyclic, saturated or unsaturated $C_1$–$C_6$ alkyl radical; an amino (—$NH_2$) radical; a carboxylic acid (—COOH) radical; a $C_1$–$C_{10}$ alkylamino radical; a $C_1$–$C_{10}$ acylamino radical;
$R''^1$, $R''^2$, $R''^3$ and $R''^4$, which may be identical or different, represent: a hydrogen atom; a linear or branched, saturated or unsaturated $C_1$–$C_4$ alkyl radical, the arrows indicating the positions of the substitutions;
k is an integer, preferably 0 or 1.
Preferably, A is chosen from the following groups:
—$CH_2$—$CH(CO_2H)$—NH—; —$(CH_2)_2$—$(CH_3CONH)$CH—; —$(CH_2)_3$— and —$CH_2$—$CH(NH$—$CO$—$CH_3)$—.
The compounds according to the invention can be obtained in particular by oxidation of the polymers described in patent application FR 97/04085, the content of which is incorporated by way of reference, and which are chosen from hyperbranched polymers and dendrimers, comprising functional groups corresponding to formula (II):

in which:
Y represents O or NH,
A represents a linear, branched or cyclic, saturated or unsaturated $C_1$–$C_{12}$ alkanediyl group, this group optionally being interrupted with one or more hetero atoms and/or substituted with a function chosen from amino, acylamino, carboxylic acid and ester.

The oxidation can be carried out by any known means, for example in air or using a common oxidizing agent such as hydrogen peroxide.

The oxidation step allows the formation of intramolecular and intermolecular disulphide bridges, starting with thiol functions, according to the scheme below:

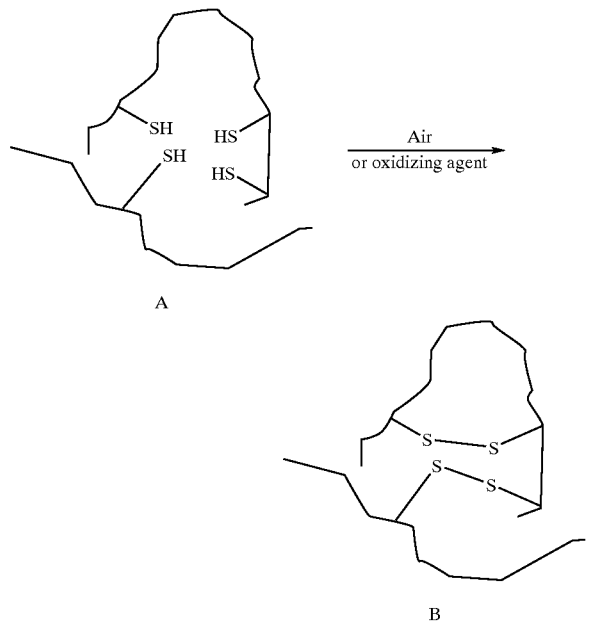

The formation of disulphide bridges brings about a "pseudo-crosslinking" of the starting compounds A, which is reflected, depending on the experimental conditions, in thickening/gelation of the medium, due to the formation of the compounds B. A gel comprising the compounds B is thus obtained directly.

The oxidation step is preferably carried out in the presence of water, for example in aqueous or aqueous-alcoholic medium.

It is thus possible to obtain gels which may be, preferably, aqueous gels or aqueous-alcoholic gels containing only water or an alcohol/water mixture, for example ethanol/water, one or more compounds B according to the invention and optionally starting compounds A that have not reacted, when the oxidation is only partially performed.

Moreover, it has been found that it is possible to incorporate water-soluble or water-insoluble additives into the aqueous or aqueous-alcoholic medium while at the same time retaining the possibility of obtaining a composition of adequate viscosity.

Among the additives which can be incorporated, mention may be made of water-soluble dyes such as fluorescein; water-soluble cosmetic or pharmaceutical active agents; water-insoluble products which have optical properties such as phosphorescence or fluorescence; pigments; fillers; sunscreens; water-insoluble cosmetic or pharmaceutical active agents.

It has moreover been found that the solid additives, pigment particles or fillers, for example, were fully dispersed homogeneously in the gel; when the viscosity of the mixture is sufficient, no decantation or release of the said particles is observed.

It is known that the properties of the gels obtained depend on the oxidation conditions, in particular the concentration of starting thiol-containing polymer, the number of thiol functions in the said thiol-containing polymer, the molar mass of the said polymer and the pH of the aqueous/aqueous-alcoholic medium before oxidation.

Thus, for example, for a poly(ethyleneimine) of given molar mass (molar mass before grafting the thiol functions), the thiol grafts being identical, it has been found that the higher the number of grafts, the more the compounds will gel at low concentration and at more acidic pH.

A thickened solution or a gel is thus obtained, which can preferably have a viscosity of between $10^{-2}$ and $10^7$ Pa·s, in particular between 10 and $10^7$ Pa·s and, for example, between $10^4$ and $10^6$ Pa·s, and which can be used, in its native form, as a cosmetic or pharmaceutical composition, or incorporated into a composition, in particular a cosmetic or pharmaceutical composition.

Depending on the oxidation conditions, it is possible for the fully oxidized mixture to remain liquid with a very small increase in viscosity (the disulphides are water-soluble at low concentration). In this case, the medium can be concentrated until a very thickened or gelled solution is obtained, depending on the use envisaged.

It is also possible to totally or partially extract the water present in the said gel, for example by drying under vacuum. The dried product thus obtained, which is generally hygroscopic, once again gives a gel when it is put back in water under suitable conditions.

When solid additives, for example such as pigment particles, are added to the medium before the oxidation step and when the gel obtained is dried, it is found that, when the dried product is rehydrated by adding water and/or alcohol, a gel having the initial characteristics is once again obtained, in particular without any "release" of the said solid particles being observed.

When the gel comprising the compounds according to the invention is intended to be used in a cosmetic or pharmaceutical composition, the said composition moreover comprises a cosmetically or pharmaceutically acceptable medium.

The said cosmetic or pharmaceutical composition can be in any form which is suitable for topical application, in particular in the form of aqueous or aqueous-alcoholic gels; in the form of water-in-oil, oil-in-water or multiple emulsions, of more or less thickened liquid consistency, such as a milk or cream; sprays or aerosol mousses; sticks or tubes; solutions or liquid dispersions.

A person skilled in the art knows how to prepare these compositions according to the usual methods, on the basis of his or her general knowledge.

In particular, these compositions can contain adjuvants usually used in the cosmetics or pharmaceuticals fields, such as oils, waxes or other common fatty substances; surfactants; moisturizers; emollients; sunscreens; hydrophilic or lipophilic active agents such as ceramides; free-radical scavengers; polymers; proteins; bactericides; sequestering agents; antidandruff agents; antioxidants; preserving agents; basifying or acidifying agents; fragrances; fillers; dyestuffs; cosmetic or pharmaceutical active agents. The amounts of these various adjuvants are those conventionally used in the fields under consideration and can readily be determined by a person skilled in the art.

Needless to say, a person skilled in the art will take care to select this or these optional additional adjuvant(s), and/or the amount thereof, such that the advantageous properties of the composition according to the invention are not, or are not substantially, adversely affected by the envisaged addition.

The compositions according to the invention are, for example, lotions, milks or creams for skincare or haircare; make-up-removing creams, lotions or milks; foundation bases; antisun or after-sun lotions, milks or creams; artificial tanning lotions, milks or creams; shaving creams or foams; aftershave lotions; body hygiene compositions such as deodorant sticks or creams; shampoos; hair products for maintaining the hairstyle or for shaping the hair such as styling gels; hair-colouring products; lipsticks; mascaras or eyeliners which may be for treatment purposes; nail varnishes or nailcare products.

The invention is illustrated in greater detail in the examples which follow.

Examples 1 to 8 describe the preparation of the starting compounds of formula (II).

Examples 9 to 16 describe the preparation of the gels according to the invention.

The gels obtained were characterized by macroscopic and microscopic observation under polarized light and by X-ray diffraction.

The results of these analyses were, respectively, isotropic behaviour and absence of crystals.

EXAMPLE 1

Branched Polyethyleneimine Polymer of Average Molecular Weight MW=2000 Containing 4 SH Functions on Average Per Unit 4.33 ml of γ-thiobutyrolactone (i.e. 50 mmol, 4 molar equivalents calculated relative to the monomer) are added, at room temperature, to 50 grams of aqueous 50% solution of polyethyleneimine of average molecular weight MW=2000, sold by the company BASF under the name Lupasol G35, under inert atmosphere at room temperature. The medium, which is initially heterogeneous, rapidly becomes homogeneous (within about 30 minutes). After stirring for 4 hours, no more γ-thiobutyrolactone is detected in the medium. The aqueous phase gives a positive reaction after revelation with sodium nitroprusside. It is thus observed that some of the initial primary amine functions are in the form of —NH—CO—$(CH_2)_3$—SH.

This aqueous phase is diluted with water qs 100 ml.

The active material content of this aqueous phase is 30.11 g/100 ml, i.e. 0.5 mol·$l^{-1}$ of thiol and 0.125 M of thiol-containing polymer. The pH is 10.3.

Molar mass of the product synthesized: 2408.64 g.$mol^{-1}$.

EXAMPLE 2

Branched Polyethyleneimine Polymer of Average Molecular Weight MW=2000 Containing 10 SH Functions on Average Per Unit 6.5 ml of γ-thiobutyrolactone (i.e. 10 molar equivalents calculated relative to the monomer) are added, at room temperature, to 30 grams of aqueous. 50% solution of polyethyleneimine of average molecular weight MW=2000 sold by the company BASF under the name Lupasol G35, under inert atmosphere at room temperature. The medium, which is initially heterogeneous, rapidly becomes homogeneous (within about 30 minutes). After stirring for 24 hours, no more γ-thiobutyrolactone is detected in the medium. The aqueous phase gives a positive reaction after revelation with sodium nitroprusside.

This aqueous phase is diluted with water qs 100 ml.

The active material content of this aqueous phase is 22.66 g/100 ml, i.e. 0.75 mol·$l^{-1}$ of thiol and 0.075 M of thiol-containing polymer. The pH is 9.6.

Molar mass of the product synthesized: 3021.6 g.$mol^{-1}$.

EXAMPLE 3

Branched Polyethyleneimine Polymer of Average Molecular Weight MW=10,000 containing 50 SH Functions on Average Per Unit 11.30 grams of 99% polyethyleneimine of average molecular weight MW=10,000 sold by the company Polysciences are diluted with 11.30 ml of water, followed by addition of 4.9 ml of γ-thiobutyrolactone (i.e. 50 molar equivalents calculated relative to the monomer), at room temperature, under inert atmosphere at room temperature. The medium, which is initially heterogeneous, rapidly becomes homogeneous (over about 30 minutes). After stirring for 20 hours, no more γ-thiobutyrolactone is detected in the medium. The aqueous phase gives a positive reaction after revelation with sodium nitroprusside. The molar mass of the product synthesized is 15,108 g.$mol^{-1}$.

This aqueous phase is diluted with water qs 100 ml and the pH is adjusted to 6.7 by addition of aqueous hydrochloric acid solution.

A homogeneous aqueous solution containing 13.67 g/100 ml of thiol-containing polymer, i.e. 0.452 mol/l, is thus obtained.

EXAMPLE 4

Branched Polyethyleneimine Polymer of Average Molecular Weight MW=10,000 Containing 20 SH Functions on Average Per Unit 10.15 grams of 99% polyethyleneimine of average molecular weight MW=10,000 sold by the company Polysciences are diluted with 10.15 ml of water, followed by addition at room temperature of 1.76 ml of γ-thiobutyrolactone (i.e. 20 molar equivalents calculated relative to the monomer) under inert atmosphere at room temperature. The medium, which is initially heterogeneous, rapidly becomes homogeneous (within about 30 minutes). After stirring for 20 hours, no more γ-thiobutyrolactone is detected in the medium.

An aqueous thiol-containing poly(ethyleneimine) solution of molar mass 12,043.2 containing on average 20 SH functions per polymer chain is thus obtained. This solution is diluted with water qs 100 ml (formation of a stable emulsion) and the pH is adjusted to 6 by addition of aqueous hydrochloric acid solution.

A homogeneous aqueous solution containing 10.51 g/100 ml of thiol-containing polymer, i.e. 0.174 mol/l, is thus obtained.

EXAMPLE 5

Branched Polyethyleneimine Polymer of Average Molecular Weight MW=25,000 Containing 50 SH Functions on Average Per Unit 12.28 g of water are added, at room temperature, to 12.28 grams of aqueous 56% solution of polyethyleneimine of average molecular weight MW=25,000, sold by the company BASF under the name Lupasol HF, followed, when the medium has once again become homogeneous, by 1.2 ml of γ-thiobutyrolactone (i.e. 50 molar equivalents calculated relative to the monomer) under inert atmosphere at room temperature. The medium, which is initially heterogeneous, rapidly becomes homogeneous (within about 30 minutes). After stirring for 24 hours, no more γ-thiobutyrolactone is detected in the medium.

An aqueous solution of thiol-containing poly (ethyleneimine) of molar mass 30,108 containing on average 50 SH functions per polymer chain is thus obtained.

19.60 g of this solution are diluted with water qs 25 ml. An aqueous solution containing 25 g/100 ml of thiol-containing polymer, i.e. 0.415 mol/l of thiol and 8.30 mmol/l of thiol-containing polymer, is thus obtained. The pH of this solution is 10.65.

EXAMPLE 6

Branched Polyethyleneimine Polymer of Average Molecular Weight MW=25,000 Containing 125 SH Functions on Average Per Unit 22.43 g of water and then 5.44 ml of γ-thio-butyrolactone (i.e. 125 molar equivalents calculated relative to the monomer) are added, at room temperature, to 22.43 grams of aqueous 56% solution of polyethyleneimine of average molecular weight MW=25,000, sold by the company BASF under the name Lupasol HF, under inert atmosphere at room temperature. The medium, which is initially heterogeneous, rapidly becomes homogeneous (within about 30 minutes). After stirring for 24 hours, no more γ-thiobutyrolactone is detected in the medium. An aqueous solution of thiol-containing poly(ethyleneimine) of molar mass 37,770, containing on average 125 SH functions per polymer chain, is thus obtained.

32.080 g of this solution are diluted with water qs 50 ml. An aqueous solution containing 25 g/100 ml of thiol-containing polymer, i.e. 0.827 mol/l of thiol and 6.619 mmol/l of thiol-containing polymer, is thus obtained. The pH of this solution is 9.96.

EXAMPLE 7

Preparation of the Thiol-containing Dendrimer: Starburst Dendrimer (PAMAM) with an Ethylenediamine Core of Generation 1 Containing 8 SH Functions at the Surface 1.35 ml of γ-thiobutyrolactone (i.e. 1 equivalent calculated relative to all of the primary amine functions) are added to 5 grams of an aqueous solution containing 55.7 g/100 g of starburst dendrimer (PAMAM) with an ethylenediamine core of generation 1 (8 $NH_2$ functions at the surface) diluted with 5 ml of water, under inert atmosphere at room temperature. The medium, which is heterogeneous on addition, rapidly becomes homogeneous after 1 hour.

After stirring for 48 hours, only traces of γ-thiobutyrolactone are detected in the medium. The mixture is washed three times with 10 ml of diethyl ether (ether is added to the medium, which is stirred for 10 minutes and then left to stand and the ether phase is then separated out). Nitrogen is bubbled into the aqueous phase thus obtained to remove all traces of ether.

The aqueous solution thus obtained is analysed by NMR. It is thus shown that all the initial primary amine functions are in the form —NH—CO—$(CH_2)_3$—SH.

The active material content of this aqueous phase is 37.76 g/100 g, i.e. 134.42 meq SH/100 g, pH=8.8.

The dendrimer thus obtained (molar mass 2247.16) is used in aqueous solution without further modification.

EXAMPLE 8

Branched Poly(ethyleneimine) Polymer of Average Molecular Weight 2000 Containing 11.09 SH Functions on Average Per Unit 12 ml of γ-thiobutyrolactone (i.e. 11.09 equivalents calculated relative to the monomer) are added, at room temperature, to 50 g of aqueous 50% solution of poly (ethyleneimine) of MW=2000, sold by BASF under the trade name Lupasol G35, under inert atmosphere at room temperature (slightly exothermic addition). The medium, which is heterogeneous on addition, rapidly becomes homogeneous (within about 30 minutes).

After stirring for 16 hours, the reaction is complete (no more γ-thiobutyrolactone is detected in the medium and the aqueous phase gives a positive reaction after revelation with sodium nitroprusside). It is thus shown that some of the initial amine functions are in the form —N—CO—$(CH_2)_3$—SH.

This aqueous phase can be diluted with water qs 100 ml.

The active material content of this aqueous phase is 39.16 g/100 ml, i.e. 1.386 mol.l$^{-1}$ of thiol and the pH is 10.15. The polymer thus obtained can be used in aqueous solution without further modification.

Average molar mass of the product synthesized: 3132.95 g.mol$^{-1}$.

EXAMPLE 9

Preparation of Aqueous Gels from Thiol-containing Poly(ethyleneimine) According to Example 1 a) "Simple" Aqueous Gels

Starting with the solution containing 30.11 g/100 ml prepared in Example 1, various solutions are prepared by dilution with water and/or acidification with aqueous hydrochloric acid solution.

Their characteristics are as follows:

| Solution | pH | Concentration of thiol-containing polymer | Concentration of thiol |
|---|---|---|---|
| 1 | 10.3 | 0.125M<br>30.11 g/100 ml | 0.500 mol/l |
| 2 | 9.0 | 0.102M<br>24.56 g/100 ml | 0.408 mol/l |

A few millilitres of solutions 1 and 2 are oxidized with the theoretical amount of 6% aqueous hydrogen peroxide solution added (i.e. 0.5 times the number of thiol functions to be oxidized to disulphide), with vigorous stirring.

Solutions 1 and 2 lead instantaneously to fairly hard transparent colourless gels.

b) Aqueous Gels Containing a Phosphorescent Inorganic Pigment

Starting with solution 1 prepared above, various samples containing copper-doped zinc sulphide sold under the name Green LBY 2330 (RN=[68611-70-1]) are prepared according to the table below:

| Solution | % of pigment |
|---|---|
| 3 | 2 |
| 4 | 5 |
| 5 | 10 |

The % of pigment is calculated by weight relative to the weight of thiol-containing polymer.

The samples are vortexed and then treated with ultrasound, after which a few millilitres of solution are oxidized with the theoretical amount of 6% aqueous hydrogen peroxide solution added (i.e. 0.5 times the number of thiol functions to be oxidized to disulphide) with vigorous stirring (vortex).

Under these conditions, solutions 3, 4 and 5 lead instantaneously to fairly hard, very pale yellow gels which are phosphorescent throughout the mass of the gel. The phosphorescence is proportionately more intense the larger the amount of pigment. All the pigment particles are distributed uniformly in the mass of the gel.

EXAMPLE 10

Preparation of Aqueous Gels Starting with Thiol-containing Poly(ethyleneimine) According to Example 2 a) "Simmple" Aqueous Gels

Starting with the solution containing 22.66 g/100 ml prepared in Example 2, various solutions are prepared by dilution with water and/or acidification cation with aqueous hydrochloric acid solution.

Their characteristics are as follows:

| Solution | pH | Concentration of thiol-containing polymer | Concentration of thiol |
|---|---|---|---|
| 6 | 9.6 | 0.075M<br>22.6 g/100 ml | 0.750 mol/l |
| 7 | 8.9 | 69.70 mM<br>21.06 g/100 ml | 0.697 mol/l |
| 8 | 8.0 | 63.56 mM<br>19.20 g/100 ml | 0.635 mol/l |
| 9 | 7.0 | 59.71 mM<br>18.04 g/100 ml | 0.597 mol/l |
| 10 | 5.95 | 57.16 mM<br>17.27 g/100 ml | 0.571 mol/l |

A few millilitres of solutions 6 to 10 are oxidized with the theoretical amount of 6% aqueous hydrogen peroxide solution added with vigorous stirring.

Solutions 6 to 10 lead instantaneously to gels.
Solutions 6 and 7 lead to opaque white gels.
Gels 8, 9 and 10 are clear, colourless and transparent.

The aqueous solutions 6 to 10 can be diluted with water according to the indications in the table below:

| Solution | pH before dilution | Concentration of thiol-containing polymer | Concentration of thiol |
|---|---|---|---|
| 11 | 9.6 | 0.03M<br>9.06 g/100 ml | 0.300 mol/l |
| 12 | 8.9 | 34.85 mM<br>10.53 g/100 ml | 0.349 mol/l |
| 13 | 8.0 | 42.37 mM<br>12.80 g/100 ml | 0.423 mol/l |
| 14 | 7.0 | 39.80 mM<br>12.03 g/100 ml | 0.380 mol/l |
| 14a | 7.0 | 33.17 mM<br>10.02 g/100 ml | 0.332 mol/l |
| 15 | 5.95 | 38.10 mM<br>11.51 g/100 ml | 0.381 mol/l |

A few millilitres of solution are oxidized he theoretical amount of 6% aqueous hydrogen de solution added with vigorous stirring.

Solution 11 leads instantaneously to a whitish, relatively non-opaque gel.

Solutions 13 and 14 lead to clear, colourless, transparent gels.

Solutions 12 and 15 lead to clear, colourless, transparent, slightly viscous gels.

The gel obtained with solution 14a has a coefficient of viscosity associated with the permanent flow obtained by flow experiments at equilibrium, of $5 \times 10^5$ Pa·s.

For comparative purposes, solution 14a which is not oxidized but diluted with a volume of water equal to the volume of oxidizing agent added to form the gel, has a coefficient of viscosity associated with the permanent flow obtained by flow experiments at equilibrium, of $1.2 \times 10^{-3}$ Pa·s.

b) Aqueous Gels Containing a Phosphorescent Inorganic Pigment

Starting with solutions 8 and 10 prepared above, various samples are prepared containing copper-doped zinc sulphide sold under the name Green LBY 2330, according to the table below:

| Solution | pH | Concentration of thiol-containing polymer | Concentration of thiol (mol/l) | % of pigment |
|---|---|---|---|---|
| 16 | 8.01 | 63.56 mM<br>19.20 g/100 ml | 0.635 | 2 |
| 17 | 8.01 | 63.56 mM<br>19.20 g/100 ml | 0.635 | 5 |
| 18 | 8.01 | 63.56 mM<br>19.20 g/100 ml | 0.635 | 10 |
| 19 | 10.3 | 57.16 mM<br>17.27 g/100 ml | 0.571 | 2 |
| 20 | 10.3 | 57.16 mM<br>17.27 g/100 ml | 0.571 | 5 |
| 21 | 10.3 | 57.16 mM<br>17.27 g/100 ml | 0.571 | 10 |

The samples are stirred by vortexing and then by ultrasound, after which a few millilitres of solution are oxidized with the theoretical amount of 6% aqueous hydrogen peroxide solution added with vigorous stirring.

Solutions 16, 17 and 18 lead instantaneously to fairly hard very pale yellow gels which are phosphorescent throughout the mass of the gel. The phosphorescence is proportionately more intense the larger the amount of pigment. All the pigment particles are distributed uniformly in the mass of the gel.

Solutions 19, 20 and 21 lead to gels after 30 seconds to 2 minutes; the medium is thus maintained under vigorous stirring alternated with ultrasound treatment until it has gelled. Fairly hard very pale yellow gels which are phosphorescent throughout the mass of the gel are obtained. All the pigment particles are distributed uniformly in the mass of the gel.

c) Aqueous-alcoholic Gels

Starting with the solution containing 22.66 g/100 ml of thiol-containing polymer prepared according to Example 2, a solution containing 19.536 g/100 ml of thiol-containing polymer at pH 8.97 is prepared by acidification with aqueous approximately 4 N hydrochloric acid solution.

0.5 ml of absolute ethanol is added to 1 ml of this aqueous solution. Oxidation is carried out with 180 μl (microlitres) of 1.8 M aqueous hydrogen peroxide solution.

The corresponding aqueous-alcoholic gel is obtained instantaneously.

EXAMPLE 11

Preparation of Aqueous Gels Starting with Thiol-containing Poly(ethyleneimine) According to Example 3

Starting with the solution containing 13.67 g/100 ml prepared according to Example 3, an aqueous gel is prepared by oxidizing with the theoretical amount of 6% aqueous hydrogen peroxide solution added with vigorous stirring (i.e. 0.5 times the number of thiol functions to be oxidized to disulphide). A clear, colourless, transparent gel is obtained.

EXAMPLE 12

Preparation of Aqueous Gels from Thiol-containing Poly(ethyleneimine) According to Example 4

Starting with the solution containing 10.51 g/100 ml prepared according to Example 4, an aqueous gel is prepared by oxidizing with the theoretical amount of 6% aqueous hydrogen peroxide solution added with vigorous stirring (i.e. 0.5 times the number of thiol functions to be oxidized to disulphide).

A clear, colourless, transparent gel is obtained 1 to 2 minutes after addition of the oxidizing agent.

EXAMPLE 13

Preparation of Aqueous Gels Starting with Thiol-containing Poly(ethyleneimine) According to Example 5 a) "Simple" Aqueous Gels

Starting with the solution containing 25 g/100 ml prepared in Example 5, various solutions are prepared by dilution with water and/or acidification with aqueous hydrochloric acid solution.

The characteristics are as follows:

| Solution | pH | Concentration of thiol-containing polymer | Concentration of thiol (mol/l) |
|---|---|---|---|
| 24 | 10.65 | 8.303 mM<br>25 g/100 ml | 0.415 |
| 25 | 8.9 | 6.323 mM<br>19.05 g/100 ml | 0.316 |
| 26 | 7.9 | 5.641 mM<br>16.98 g/100 ml | 0.282 |
| 27 | 6.9 | 5.289 mM<br>15.923 g/100 ml | 0.264 |
| 28 | 5.7 | 4.942 mM<br>14.881 g/100 ml | 0.247 |

A few millilitres of solution are oxidized with the theoretical amount of 6% aqueous hydrogen peroxide solution added with vigorous stirring (i.e. 0.5 times the number of thiol functions to be oxidized to disulphide).

Solutions 25 to 28 lead to clear, colourless, transparent gels: instantaneously for Examples 25 and 26, after 30 seconds for Example 27 and after 2 minutes approximately for Example 28 for which the gel obtained is still viscous.

The aqueous solutions 24, 25, 26 and 27 can be diluted with water according to the indications of the table below:

| Solution | pH before dilution | Concentration of thiol-containing polymer | Concentration of thiol (mol/l) |
|---|---|---|---|
| 29 | 10.65 | 2.768 mM<br>8.33 g/100 ml | 0.138 |
| 30 | 8.9 | 4.220 mM<br>12.70 g/100 ml | 0.211 |
| 31 | 7.9 | 3.760 mM<br>11.32 g/100 ml | 0.188 |
| 32 | 6.9 | 4.407 mM<br>13.27 g/100 ml | 0.220 |

A few millilitres of solution are oxidized with the theoretical amount of 6% aqueous hydrogen peroxide solution added with vigorous stirring.

Solutions 29 and 30 lead instantaneously to clear, colourless, transparent gels that are slightly viscous.

Solutions 31 and 32 lead, after 30 seconds to 1 minute, to clear, colourless, transparent gels that are slightly viscous.

b) Aqueous Gels Containing Solid Products that are Insoluble in the Medium

Starting with solutions 26, 27 and 28 prepared above, various samples are prepared according to the table below, containing:

product A: phosphorescent pigment (copper-doped zinc sulphide sold under the name Green LBY 2330)

product B: blue-coloured pigment (Ultramarine Blue, CI 77007)

product C: yellow-coloured pigment (FD&C Yellow No 5 Aluminum Lake, CI 19140:1)

product D: water-insoluble red dye (D&C Red No 36, CI 12085)

product E: water-insoluble fluorescent product (trans, trans-1,4-bis[2-(3,4,5-trimethoxyphenyl)vinyl]-bezene)

| Solution | pH | Concentration of thiol-containing polymer | Concentration of thiol (mol/l) | % of pigment |
|---|---|---|---|---|
| 33 | 5.7 | 4.942 mM<br>14.88 g/100 ml | 0.247 | 5% product A |
| 34 | 7.9 | 5.641 mM<br>16.98 g/100 ml | 0.282 | 5% product B |
| 35 | 7.9* | 3.761 mM<br>11.32 g/100 ml | 0.188 | 2% product C |
| 36 | 6.9 | 5.289 mM<br>15.92 g/100 ml | 0.264 | 1% product D |
| 37 | 5.7 | 4.942 mM<br>14.88 g/100 ml | 0.247 | 5% product E |

*pH of the solution before dilution with ½ volume of water

The samples are stirred by vortexing and with ultrasound, after which a few millilitres of solution are oxidized with the theoretical amount of 6% aqueous hydrogen peroxide solution added with vigorous stirring (i.e. 0.5 times the number of thiol functions to be oxidized to disulphide).

Solutions 33 to 37 lead instantaneously to coloured gels or to gels having specific optical properties as indicated below:

solution 33: almost colourless very pale yellow gel which is phosphorescent throughout its mass. All the pigment particles are uniformly distributed in the mass of the gel.

solution 34: intense bright blue gel. All the pigment particles are uniformly distributed in the mass of the gel.

solution 35: intense bright yellow gel. All the pigment particles are uniformly distributed in the mass of the gel.

solution 36: intense bright red gel. All the dye particles are uniformly distributed in the mass of the gel.

solution 37: "fluo type" green-yellow gel, which is transparent and fluorescent in the blue region under UV radiation at 365 nm. All the particles of product E are distributed uniformly in the mass of the gel. Fluorescence throughout the mass of the gel.

c) Aqueous Gels Containing Water-soluble Dyes

Starting with solutions 26, 27 and 28 prepared above, various samples are prepared, according to the table below, containing:

dye F=fluorescein, sodium salt (Acid Yellow 73, Color Index 45350)

dye G=Rhodamine B (RN=[81-88-9])

dye H=Orange G (Acid Orange 10, Color Index 16230)

| Solution | pH | Concentration of thiol-containing polymer | Concentration of thiol (mol/l) | % of colorant |
|---|---|---|---|---|
| 38 | 7.9* | 4.942 mM 14.88 g/100 ml | 0.247 | 0.2% product F |
| 39 | 6.9** | 5.641 mM 16.98 g/100 ml | 0.282 | 0.1% product G |
| 40 | 5.7 | 3.761 mM 11.32 g/100 ml | 0.188 | 0.2% product H |
| 41 | 5.7 | 5.289 mM 15.92 g/100 ml | 0.264 | 0.01% product F |

*pH of the solution before dilution with ½ volume of aqueous dye solution
**pH of the solution before dilution with ⅕ volume of aqueous dye solution The samples are stirred by vortexing and with ultrasound, after which a few millilitres of solution are oxidized with the theoretical amount of 6% aqueous hydrogen peroxide solution added with vigorous stirring (i.e. 0.5 times the number of thiol functions to be oxidized to disulphide).

Solutions 38 to 41 lead instantaneously to gels coloured as indicated below:

solution 38: intense fluo bright yellow gel solution 39: intense fuchsia pink gel solution 40: slightly pale orange gel solution 41: very pale yellow gel

EXAMPLE 14

Preparation of Aqueous Gels Starting with thiol-Containing Poly(ethyleneimine) According to Example 6 a) "Simple" Aqueous Gels

Starting with the solution containing 25 g/100 ml prepared in Example 6, various solutions are prepared by dilution with water and/or acidification with aqueous hydrochloric acid solution.

Their characteristics are as follows:

| Solution | pH | Concentration of thiol-containing polymer | Concentration of thiol (mol/l) |
|---|---|---|---|
| 42 | 8.9 | 5.571 mM 21.04 g/100 ml | 0.696 |
| 43 | 8.0 | 5.187 mM 19.59 g/100 ml | 0.648 |
| 44 | 6.9 | 4.896 mM 18.49 g/100 ml | 0.612 |
| 45 | 5.8 | 4.755 mM 17.960 g/100 ml | 0.594 |
| 46 | 5.0 | 4.583 mM 17.313 g/100 ml | 0.573 |

A few millilitres of solution are oxidized with the theoretical amount of 6% aqueous hydrogen peroxide solution added with vigorous stirring (i.e. 0.5 times the number of thiol functions to be oxidized to disulphide).

Solutions 43 to 46 lead to clear, colourless, transparent gels: instantaneously for Examples 42 and 43, after about 10 seconds for Example 44, after 30 seconds to 1 minute for Example 45 and after 5 minutes approximately for Example 46.

Oxidation of solution 42 leads to a slightly opaque, whitish gel.

The aqueous solutions 42 to 45 can be diluted with water according to the indications below:

| Solution | pH before dilution | Concentration of thiol-containing polymer | Concentration of thiol (mol/l) |
|---|---|---|---|
| 47 | 8.9 | 2.786 mM 10.52 g/100 ml | 0.348 |
| 48 | 8.0 | 2.593 mM 9.796 g/100 ml | 0.324 |
| 49 | 6.9 | 3.497 mM 13.21 g/100 ml | 0.437 |
| 50 | 5.8 | 3.962 mM 14.97 g/100 ml | 0.495 |
| 50a | 8.9 | 3.34 mM 12.63 g/100 ml | 0.418 |

A few millilitres of solution are oxidized with the theoretical amount of 6% aqueous hydrogen peroxide solution added with vigorous stirring (i.e. 0.5 times the number of thiol functions to be oxidized to disulphide).

Solutions 48 to 50a lead to clear, colourless, transparent gels: after a few seconds for Example 50a; after about 1 minute for Examples 48 and 49, and after 5 minutes for Example 50.

After oxidation, solution 47 becomes viscous in 10–20 seconds.

The viscous mixture obtained with solution 47 has a coefficient of viscosity associated with the permanent flow obtained by flow experiments at equilibrium of $4.5 \times 10^{-2}$ Pa·s.

For comparative purposes, solution 47 not oxidized but diluted with a volume of water equal to the volume of oxidizing agent added to thicken it, has a coefficient of viscosity associated with the permanent flow obtained by flow experiments at equilibrium of $1.9 \times 10^{-3}$ Pa·s.

The gel obtained with solution 50a has a coefficient of viscosity associated with the permanent flow obtained by flow experiments at equilibrium of about $2 \times 10^5$ Pa·s.

b) Aqueous Gels Containing Solid Products that are Insoluble in the Medium

Starting with solutions 42, 43, 44, 45 and 46 prepared above, various samples are prepared, containing:

product A: phosphorescent pigment (copper-doped zinc sulphide sold under the name Green LBY 2330)

product I: blue-coloured pigment (FD&C Blue No 1 Aluminium Lake, Color Index 42090:2)

product J: green-coloured pigment (Chromium Hydroxide Green, Color Index 77289)

product K: red-coloured pigment (D&C Red No 7 Calcium Lake)

product E: water-insoluble fluorescent product (trans, trans-1,4-bis[2-(3,4,5-trimethoxyphenyl)vinyl]-benzene)

| Solution | pH | Concentration of thiol-containing polymer | Concentration of thiol (mol/l) | % of pigment |
|---|---|---|---|---|
| 51 | 8.94* | 2.786 mM 10.52 g/100 ml | 0.348 | 2% product I |
| 52 | 8.0* | 2.594 mM 9.797 g/100 ml | 0.324 | 1.4% product J |
| 53 | 6.9** | 4.080 mM 15.41 g/100 ml | 0.510 | 3% product K |
| 54 | 5.8** | 3.962 mM 14.966 g/100 ml | 0.495 | 3% product E |
| 55 | 5.0 | 4.584 mM 17.31 g/100 ml | 0.573 | 5% product A |

*pH of the solution before dilution with 1 volume of water
**pH of the solution before dilution with ⅕ volume of water The samples are stirred by vortexing and with ultrasound, after which a few millilitres of solution are oxidized with the theoretical amount of 6% aqueous hydrogen peroxide solution added with vigorous stirring (i.e. 0.5 times the number of thiol functions to be oxidized to disulphide).

Solutions 51 to 55 lead instantaneously to coloured gels or to gels which have specific optical properties, as indicated below:

solution 51: intense blue gel. All the pigment particles are distributed uniformly in the mass of the gel.

solution 52: intense green gel. All the pigment particles are distributed uniformly in the mass of the gel.

solution 53: intense red gel. All the pigment particles are distributed uniformly in the mass of the gel.

solution 54: "fluo type" green-yellow gel, which is transparent and fluorescent in the blue region under UV irradiation at 365 nm. All the pigment particles are distributed uniformly in the mass of the gel. Fluorescence throughout the mass of the gel.

solution 55: almost colourless very pale yellow gel which is phosphorescent throughout its mass. All the pigment particles are distributed uniformly in the mass of the gel.

c) Aqueous Gels Containing Water-soluble Dyes

Starting with solutions 42, 43, 44, 45 and 46 prepared above, various samples are prepared, containing:

dye F=fluorescein, sodium salt (Acid Yellow 73, Color Index 45350)

dye G=Rhodamine B (RN=[81-88-9])

dye H=Orange G (Acid Orange 10, Color Index 16230)

| Solution | pH | Concentration of thiol-containing polymer | Concentration of thiol (mol/l) | % of colorant |
|---|---|---|---|---|
| 56 | 8.9* | 2.786 mM 10.52 g/100 ml | 0.348 | 0.1% dye G |
| 57 | 8.0* | 2.594 mM 9.80 g/100 ml | 0.324 | 0.2% dye F |
| 58 | 6.9** | 3.917 mM 14.79 g/100 ml | 0.489 | 0.05% dye G |
| 59 | 5.8*** | 3.962 mM 14.97 g/100 ml | 0.495 | 2% dye F |
| 60 | 5.0 | 4.584 mM 17.31 g/100 ml | 0.573 | 1% dye H |

*pH of the solution before dilution with 1 volume of aqueous dye solution
**pH of the solution before dilution with ½ volume of aqueous dye solution
***pH of the solution before dilution with ⅕ volume of aqueous dye solution The samples are stirred by vortexing and with ultrasound, after which a few millilitres of solution are oxidized with the theoretical amount of 6% aqueous hydrogen peroxide solution added with vigorous stirring (i.e. 0.5 times the number of thiol functions to be oxidized to disulphide).

Solutions 56 to 60 lead to gels coloured as indicated below:

solution 56: intense fuchsia pink gel solution 57: intense fluo yellow gel solution 58: intense fuchsia pink gel solution 59: intense fluo yellow gel solution 60: pale orange gel

EXAMPLE 15

Preparation of Aqueous Gels Starting with the Thiol-containing Dendrimer According to Example 7

Starting with the solution containing 37.76 g/100 g prepared according to Example 7, various solutions are prepared by dilution with water and/or acidification with aqueous hydrochloric acid solution.

Their characteristics are as follows:

| Solution | pH | Concentration of thiol-containing dendrimer | Concentration of thiol (mmol/100 g) |
|---|---|---|---|
| 61 | 8.8 | 16.80 mmol/100 g 37.76 g/100 g | 134.42 |
| 62 | 8.8* | 11.20 mmol/100 g 25.17 g/100 g | 89.62 |
| 63 | 7.15 | 15.85 mmol/100 g 35.62 g/100 g | 126.82 |
| 64 | 7.7 | 8.20 mmol/100 g 18.42 g/100 g | 65.57 |

*before dilution with water

A few millilitres of solution are oxidized with the theoretical amount of 6% aqueous hydrogen peroxide solution added with vigorous stirring (vortex), i.e. 0.5 times the number of thiol functions to be oxidized to disulphide.

Solutions 61 and 62 lead to opaque white gels that are very hard (instantaneous for Example 61; after a few seconds for Example 62).

Solution 64 leads to an opaque white gel after a few minutes.

Solution 63 leads, after a few minutes, to a fairly rigid clear, colourless, transparent gel.

EXAMPLE 16

Preparation of Aqueous Gels Starting with Thiol-containing poly(ethyleneimine) According to Example 8 a) "Simple" Aqueous Gels

Starting with the solution containing 39.16 g/100 ml prepared in Example 8, various solutions are prepared by dilution with water and/or acidification with an aqueous hydrochloric acid solution.

Their characteristics are as follows:

| Solution | pH | Concentration of thiol-containing polymer | Concentration of thiol |
|---|---|---|---|
| 65 | 9.04 | 101.128 mM<br>31.683 g/100 ml | 1.121 mol/l |
| 66 | 8.01 | 89.027 mM<br>27.892 g/100 ml | 0.987 mol/l |
| 67 | 7.02 | 82.668 mM<br>25.899 g/100 ml | 0.917 mol/l |
| 68 | 6.04 | 78.121 mM<br>24.475 g/100 ml | 0.866 mol/l |

A few millilitres of solutions 65 to 68 are oxidized with the theoretical amount of 6% aqueous hydrogen peroxide solution added with vigorous stirring (vortex), i.e. 0.5 times the number of thiol functions to be oxidized to disulphide.

Solution 65 leads instantaneously to a clear, colourless, transparent gel. Solutions 66, 67 and 68 lead to clear, transparent, colourless gels after respective times of 5–10 seconds, 10–20 seconds and a few minutes.

The gel obtained with solution 67 has a coefficient of viscosity associated with the permanent flow obtained by flow experiments at equilibrium of $3.5 \times 10^4$ Pa·s.

For comparative purposes, solution 67 not oxidized but diluted with a volume of water equal to the volume of oxidizing agent added to form the gel has a viscosity of $2 \times 10^{-3}$ Pa·s.

Solutions 65 to 67 can be diluted with water according to the indications of the table below:

| Solution | pH before dilution | Concentration of thiol-containing polymer | Concentration of thiol |
|---|---|---|---|
| 69 | 9.04 | 21.1218 g/100 ml<br>67.4185 mM | 0.748 M |
| 70 | 9.04 | 15.0870 g/100 ml<br>48.1561 mM | 0.534 M |
| 71 | 9.04 | 13.7751 g/100 ml<br>43.9686 mM | 0.488 M |
| 72 | 9.04 | 12.6731 g/100 ml<br>40.4511 mM | 0.449 M |
| 73 | 8.01 | 13.9458 g/100 ml<br>44.51353 mM | 0.494 M |
| 74 | 8.01 | 12.678 g/100 ml<br>40.4668 mM | 0.449 M |
| 75 | 8.01 | 11.6216 g/100 ml<br>37.0946 mM | 0.411 M |
| 76 | 7.02 | 21.5829 g/100 ml<br>68.890 mM | 0.764 M |

-continued

| Solution | pH before dilution | Concentration of thiol-containing polymer | Concentration of thiol |
|---|---|---|---|
| 77 | 7.02 | 18.4996 g/100 ml<br>59.0486 mM | 0.655 M |
| 78 | 7.02 | 17.2663 g/100 ml<br>55.112 mM | 0.611 M |
| 79 | 7.02 | 16.1871 g/100 ml<br>51.667 mM | 0.573 M |
| 80 | 7.02 | 14.388 g/100 ml<br>45.927 mM | 0.509 M |

A few millilitres of solution are oxidized with the theoretical amount of 6% aqueous hydrogen peroxide solution added with vigorous stirring (vortex).

Solution 69 leads instantaneously to a clear, colourless, transparent gel.

Solutions 70 to 80 lead to clear, colourless, transparent gels in times ranging from a few seconds to a few minutes.

b) "Simple" Aqueous-alcoholic Gels

Solutions 66 and 67 can be diluted with absolute ethanol according to the indications in the table below:

| Solution | pH before dilution | Dilution with ethanol | Concentration of thiol-containing polymer | Concentration of thiol |
|---|---|---|---|---|
| 81 | 8.01 | 10 ml sol.66 +<br>12 ml EtOH | 12.678 g/100 ml<br>40.4668 mM | 0.4488 M |
| 82 | 7.02 | 10 ml sol.67 +<br>5 ml EtOH | 17.2663 g/100 ml<br>55.112 mM | 0.6112 M |

A few millilitres of solution are oxidized with the theoretical amount of 6% aqueous hydrogen peroxide solution added with vigorous stirring (vortex).

Under these conditions, solutions 81 and 82 lead to clear, colourless, transparent gels which are similar in appearance, respectively, to the gels obtained with the aqueous solutions 74 and 78.

What is claimed:

1. A compound chosen from hyperbranched polymers and dendrimers comprising at least one group of formula (I):

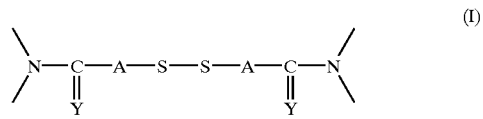

wherein:

Y is chosen from an oxygen atom and an NH group, and

A is chosen from linear, branched, and cyclic, saturated and unsaturated, $C_1$–$C_{12}$ alkanediyl groups, said groups being substituted with at least one group chosen from:
    amino;
    —NH—CO—R in which R is chosen from linear, branched, and cyclic, saturated and unsaturated, $C_1$–$C_{10}$ alkyl groups;
    carboxylic acid; and
    —COOR in which R is chosen from linear, branched, and cyclic, saturated and unsaturated, $C_1$–$C_{10}$ alkyl groups, and wherein A is optionally interrupted by at least one heteroatom.

2. A compound according to claim 1, wherein the compound is a dendrimer.

3. A compound according to claim 1, wherein the compound is a hyperbranched polymer.

4. A compound according to claim 3, wherein the hyperbranched polymer is a polyethyleneimine.

5. A compound according to claim 1, wherein Y is an oxygen atom.

6. A compound according to claim 1, wherein A is chosen from (a) —CHR$^1$—CHR$^2$—CHR$^3$—

(b) —CHR$^{'1}$—CHR$^{'2}$—CHR$^{'3}$—CHR$^{'4}$—

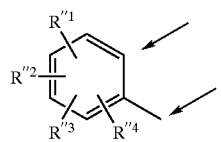
(c)

(d) —(CHR$^{''1}$)$_k$—(CHR$^{''2}$)—CH(CO$_2$H)—NH— wherein:
R$^1$, R$^2$, R$^3$, R$^{'1}$, R$^{'2}$, R$^{'3}$, R$^{'4}$, R$^{'''1}$, and R$^{'''2}$, which are identical or different, are independently chosen from:
a hydrogen atom;
linear, branched, and cyclic, saturated and unsaturated, C$_1$–C$_6$ alkyl radicals;
an amino radical;
a carboxylic acid radical;
C$_1$–C$_{10}$ alkylamino radical; and
C$_1$–C$_{10}$ acylamino radical;
R$^{''1}$, R$^{''2}$, R$^{''3}$, and R$^{''4}$, which are identical or different, are independently chosen from:
a hydrogen atom; and
linear, branched, and cyclic, saturated and unsaturated, C$_1$–C$_4$ alkyl radicals, the arrows indicating the position of substitution;
k is an integer chosen from 0 and 1.

7. A compound according to claim 1, wherein A is chosen from:
—CH$_2$—CH(CO$_2$H)—NH—;
—(CH$_2$)$_2$—(CH$_3$CONH)CH—; and
—CH$_2$—CH(NH—CO—CH$_3$)—.

8. A process for preparing a compound according to claim 19, comprising oxidizing a polymer chosen from hyperbranched polymers and dendrimers comprising at least one group of formula (II):

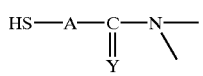
(II)

wherein:
Y is chosen from an oxygen atom and an NH group, and
A is chosen from linear, branched, and cyclic, saturated and unsaturated, C$_1$–C$_{12}$ alkanediyl groups, said groups being substituted with at least one group chosen from:
amino;
—NH—CO—R in which R is chosen from linear, branched, and cyclic, saturated and unsaturated, C$_1$–C$_{10}$ alkyl groups;
carboxylic acid; and
—COOR in which R is chosen from linear, branched, and cyclic, saturated and unsaturated, C$_1$–C$_{10}$ alkyl groups under conditions sufficient to prepare said compound.

9. A process according to claim 8, wherein the oxidation is performed in air.

10. A process according to claim 8, wherein the oxidation is performed with an oxidizing agent.

11. A process according to claim 10, wherein the oxidizing agent is hydrogen peroxide.

12. A process according to claim 8, wherein the oxidation is performed in the presence of water.

13. A process according to claim 8, wherein the oxidation is performed in an aqueous or aqueous-alcoholic medium.

14. A process according to claim 13, wherein additives are incorporated into the aqueous or aqueous-alcohol medium.

15. A process according to claim 14, wherein the additives are chosen from water-soluble dyes, cosmetic active agents, pharmaceutical active agents, sunscreens, pigments, fillers, and products having optical properties.

16. A process according to claim 15, wherein the dyes include fluorescein.

17. A process according to claim 15, wherein the optical properties are phosphorescence and/or fluorescence.

18. A process for thickening a composition comprising adding to the composition an effective thickening amount of a compound chosen from hyperbranched polymers and dendrimers comprising at least one group of formula (I):

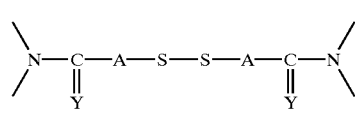
(I)

wherein:
Y is chosen from an oxygen atom and an NH group, and
A is chosen from linear, branched, and cyclic, saturated and unsaturated, C$_1$–C$_{12}$ alkanediyl groups, said groups being substituted with at least one group chosen from:
amino;
—NH—CO—R in which R is chosen from linear, branched, and cyclic, saturated and unsaturated, C$_1$–C$_{10}$ alkyl groups;
carboxylic acid; and
—COOR in which R is chosen from linear, branched, and cyclic, saturated and unsaturated, C$_1$–C$_{10}$ alkyl groups.

19. A process according to claim 18, wherein the composition is a cosmetic or pharmaceutical composition.

20. A process according to claim 19, wherein the cosmetic or pharmaceutical composition further comprises a cosmetically or pharmaceutically acceptable medium.

21. A process for converting a cosmetic or pharmaceutical composition to a gel, comprising adding an effective amount of at least one compound chosen from hyperbranched polymers and dendrimers comprising at least one group of formula (I):

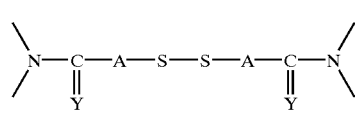
(I)

wherein:
Y is chosen from an oxygen atom and an NH group, and
A is chosen from linear, branched, and cyclic, saturated and unsaturated, C$_1$–C$_{12}$ alkanediyl groups, said groups being substituted with at least one group chosen from:
amino;
acylamino in which R is chosen from linear, branched, and cyclic, saturated and unsaturated, C$_1$–C$_{10}$ alkyl groups;

carboxylic acid; and carboxylic acid esters (—COOR) in which R is chosen from linear, branched, and cyclic, saturated and unsaturated, $C_1$–$C_{10}$ alkyl groups, to the cosmetic or pharmaceutical composition to form said gel.

22. A process according to claim 21, wherein the cosmetic or pharmaceutical composition comprises a cosmetic or pharmaceutical active agent.

23. A process according to claim 21, further comprising the step of totally or partially extracting water from the gel to form a totally or partially dried, hygroscopic product.

24. A process according to claim 23, further comprising the step of rehydrating the totally or partially dried, hygroscopic product to form a gel.

25. A cosmetic or pharmaceutical composition comprising, in a cosmetically or pharmaceutically acceptable medium, at least one compound chosen from hyperbranched polymers and dendrimers comprising at least one group of formula (I):

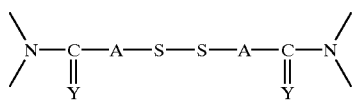

(I)

wherein:

Y is chosen from an oxygen atom and an NH group, and

A is chosen from linear, branched, and cyclic, saturated and unsaturated, $C_1$–$C_{12}$ alkanediyl groups, said groups being substituted with at least one group chosen from:
amino;
—NH—CO—R in which R is chosen from linear, branched, and cyclic, saturated and unsaturated, $C_1$–$C_{10}$ alkyl groups;
carboxylic acid; and
—COOR in which R is chosen from linear, branched, and cyclic, saturated and unsaturated, $C_1$–$C_{10}$ alkyl groups.

26. A composition according to claim 25, wherein the cosmetically or pharmaceutically acceptable medium comprises at least one fatty substance.

27. A composition according to claim 26, wherein the at least one fatty substance is chosen from oils and waxes.

28. A composition according to claim 25, further comprising at least one adjuvant chosen from surfactants, moisturizers, emollients, sunscreens, hydrophilic active agents, lipophilic active agents, free-radical scavengers, polymers, proteins, bactericides, sequestering agents, antidandruff agents, antioxidants, preserving agents, basifying agents, acidifying agents, fragrances, fillers, dyestuffs, cosmetic active agents, and pharmaceutical active agents.

29. An aqueous gel, an aqueous-alcoholic gel, a water-in-oil emulsion, an oil-in-water emulsion, a multiple emulsion, a cream, a milk, a spray mousse, an aerosol mousse, a stick, a tube, a solution, or a liquid dispersion comprising at least one compound chosen from hyperbranched polymers and dendrimers comprising at least one group of formula (I):

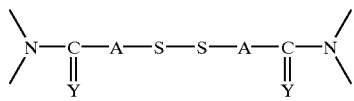

(I)

wherein:

Y is chosen from an oxygen atom and an NH group, and

A is chosen from linear, branched, and cyclic, saturated and unsaturated, $C_1$–$C_{12}$ alkanediyl groups, said groups being substituted with at least one group chosen from:
amino;
—NH—CO—R in which R is chosen from linear, branched, and cyclic, saturated and unsaturated, $C_1$–$C_{10}$ alkyl groups;
carboxylic acid; and
—COOR in which R is chosen from linear, branched, and cyclic, saturated and unsaturated, $C_1$–$C_{10}$ alkyl groups.

30. A skincare or haircare lotion, milk, or cream; a make-up-removing lotion, milk, or cream; a foundation base; an antisun or after-sun lotion, milk, or cream; an artificial tanning lotion, milk, or cream; a shaving cream or foam; an aftershave lotion; a body hygiene composition; a shampoo; a hair product for maintaining the hairstyle or for shaping the hair; a hair-coloring product; a lipstick; a mascara or eyeliner; or a nail varnish or nailcare product comprising a compound chosen from hyperbranched polymers and dendrimers comprising at least one group of formula (I):

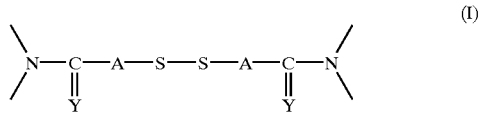

(I)

wherein:

Y is chosen from an oxygen atom and an NH group, and

A is chosen from linear, branched, and cyclic, saturated and unsaturated, $C_1$–$C_{12}$ alkanediyl groups, said groups being substituted with at least one group chosen from:
amino;
—NH—CO—R in which R is chosen from linear, branched, and cyclic, saturated and unsaturated, $C_1$–$C_{10}$ alkyl groups;
carboxylic acid; and
—COOR) in which R is chosen from linear, branched, and cyclic, saturated and unsaturated, $C_1$–$C_{10}$ alkyl groups.

31. A composition according to claim 30, wherein the body hygiene composition is a deodorant stick or cream.

32. A composition according to claim 30, wherein the hair product for maintaining the hairstyle or shaping the hair is a styling gel.

33. A composition according to claim 30, wherein the mascara or eyeliner contains a pharmaceutical active agent.

34. A composition according to claim 25, wherein the viscosity of the composition ranges from $10^{-2}$ to $10^7$ Pa·s.

35. A composition according to claim 34, wherein the viscosity of the composition ranges from 10 to $10^7$ Pa·s.

36. A composition according to claim 35, wherein the viscosity of the composition ranges from $10^4$ to $10^5$ Pa·s.

37. A process for preparing a composition according to claim 25, comprising oxidizing a composition comprising at least one polymer chosen from hyperbranched polymers and dendrimers comprising at least one group of formula (II):

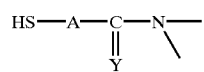 (II)

wherein:
Y is chosen from an oxygen atom and an NH group, and
A is chosen from linear, branched, and cyclic, saturated and unsaturated, $C_1$–$C_{12}$ alkanediyl groups, said groups being substituted with at least one group chosen from:

amino;

—NH—CO—R in which R is chosen from linear, branched, and cyclic, saturated and unsaturated, $C_1$–$C_{10}$ alkyl groups;

carboxylic acid; and

—COOR in which R is chosen from linear, branched, and cyclic, saturated and unsaturated, $C_1$–$C_{10}$ alkyl groups.

* * * * *

UNITED STATES PATENT AND TRADEMARK OFFICE
CERTIFICATE OF CORRECTION

PATENT NO.   : 6,475,495 B1                                              Page 1 of 1
DATED        : November 5, 2002
INVENTOR(S)  : Jean Maignan et al.

It is certified that error appears in the above-identified patent and that said Letters Patent is hereby corrected as shown below:

Title page, Item [54] and Column 1, lines 1-5,
"HYPERBRANCHED POLYMERS OR DENDRIMERS CONTAINING A PARTICULAR GROUP, PREPARATION PROCESS, USE AND COMPOSITIONS COMPRISING THEM" should read
-- HYPERBRANCHED POLYMERS OR DENDRIMERS HAVING A PARTICULAR GROUP, PREPARATION METHOD AND COMPOSITIONS CONTAINING SAME --.

Column 21,
Lines 42-43, "claim 19" should read -- claim 1 --.

Column 24,
Line 47, "–COOR)" should read -- –COOR --.

Signed and Sealed this

First Day of April, 2003

JAMES E. ROGAN
*Director of the United States Patent and Trademark Office*